US00PP12240P2

(12) United States Plant Patent
Sorensen

(10) Patent No.: US PP12,240 P2
(45) Date of Patent: Nov. 27, 2001

(54) OSTEOSPERMUM PLANT NAMED 'DONDO'

(75) Inventor: Carl Aksel Kragh Sorensen, Aabyhoj (DK)

(73) Assignee: Paul Ecke Ranch, Inc., Encinitas, CA (US)

( * ) Notice: Subject to any disclaimer, the term of this patent is extended or adjusted under 35 U.S.C. 154(b) by 0 days.

(21) Appl. No.: 09/291,104

(22) Filed: Apr. 14, 1999

(51) Int. Cl.[7] ..... A01H 5/00
(52) U.S. Cl. ..... Plt./360
(58) Field of Search ..... Plt./360

(56) References Cited

PUBLICATIONS

UPOV CD–ROM, PBR 961162, Osteospermum designated Dondo, 1996.*
UPOV CD–ROM, PBR 10846, Osteospermum designated Dondo, 1998.*

* cited by examiner

*Primary Examiner*—Bruce R. Campell
*Assistant Examiner*—Melissa L. Kimball
(74) *Attorney, Agent, or Firm*—C. A. Whealy

(57) ABSTRACT

A distinct cultivar of Osteospermum plant named 'Dondo', characterized by its upright and outwardly spreading plant habit; numerous inflorescences per plant; pink ray florets with blue disc florets; and tolerance to high temperatures.

1 Drawing Sheet

BACKGROUND OF THE INVENTION

The invention relates to a new and distinct cultivar of Osteospermum plant, botanically known as *Osteospermum ecklonis* and referred to by the cultivar name Dondo.

The new cultivar is a product of a planned breeding program conducted by the Inventor in Aabyhoj, Denmark. The objective of the breeding program was to create new Osteospermum cultivars with interesting ray floret colors.

The new cultivar originated from a cross made by the Inventor in 1995 of proprietary selection of *Osteospermum ecklonis* identified as 949343 as the female, or seed, parent and a proprietary selection of *Osteospermum ecklonis* identified as 949322 as the male, or pollen, parent. The new Osteospermum was selected by the Inventor as a flowering plant within the progeny of this cross in a controlled environment in Aabyhoj, Denmark, in 1996.

Plants of the new cultivar are different from plants of the female parent, the selection 949343, in inflorescence size and quantity of ray florets.

Plants of the new Osteospermum are different from plants of the male parent, the selection 949322, in plant habit inflorescence size and quantity of ray florets.

Asexual propagation of the new cultivar by terminal cutting at Aabyhoj, has shown that the unique features of this new Osteospermum are stable and reproduced true to type in successive generations.

SUMMARY OF THE INVENTION

The following traits have been repeatedly observed and are determined to be the unique characteristics of 'Dondo'. These characteristics in combination distinguish 'Dondo' as a new and distinct cultivar:

1. Upright and outwardly spreading plant habit.
2. Numerous inflorescences per plant.
3. Pink ray florets with blue disc florets.
4. Tolerance to high temperatures.

The new cultivar can be compared to the Osteospermum cultivar Cape Daisy Congo, disclosed in U.S. Plant Pat. No. 10,342. In side-by-side comparisons conducted in Aabyhoj, Denmark, and Encinitas, Calif., plants of the new cultivar are smaller and less vigorous; are less freely branching; have smaller inflorescences; have darker red purple ray florets that resist fading better; and are more high temperature tolerant than plants of the cultivar Cape Daisy Congo.

The cultivar Dondo has not been observed under all possible environmental conditions. The phenotype may vary somewhat with variations in environment such as temperature, daylength and light intensity, without, however, any variance in genotype.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slighty from color values cited in the detailed botanical description which more accurately describes the actual colors of the new Osteospermum.

The photograph at the top of the sheet comprises a side perspective view of a typical flowering plant of 'Dondo'.

The photograph at the bottom of the sheet is a close-up view of typical inflorescences and young and mature leaves of 'Dondo' (code number 9604 in the photograph) and 'Cape Daisy Congo' (Congo in the photograph).

DETAILED BOTANICAL DESCRIPTION

The following observations, measurements and values describe one-gallon containers of the new cultivar grown in Encinitas, Calif., under outdoor, full-sun conditions with day temperatures ranging from 20 to 27° C. and night temperatures ranging from 6 to 14° C. Plants were pinched (terminal apex removed) one time about two weeks after planting rooted cuttings. Plants used for this description were grown for about 12 to 14 weeks after planting rooted cuttings.

Color references are made to The Royal Horticultural Society Colour Chart except where general terms of ordinary dictionary significance are used.

Botanical classification: *Osteospermum ecklonis* cultivar Dondo.

Parentage:

*Female, or seed, parent*.—Proprietary selection of *Osteospermum ecklonis* identified as 949343.

*Male, or pollen, parent*.—Proprietary selection of *Osteospermum ecklonis* identified as 949322.

Propagation:

*Type*.—By terminal cuttings.

*Time to initiate roots*.—About 10 days at 18° C.

*Time to develop roots*.—About 21 days at 18° C.

*Rooting habit*.—Fibrous.

Plant description:

*Appearance*.—Perennial herbaceous container and garden plant. Broad inverted triangle. Upright, outwardly spreading with rounded canopy. Moderate branching with about five primary and about five to seven secondary branches.

*Vigor*.—Moderate.

*Plant height*.—About 30 cm.

*Plant spread*.—About 50 cm.

*Lateral branch description*.—Length: About 13 to 18 cm. Diameter: Primary, about 1 cm; secondary, about 4 mm. Internode length: About 1 to 2.5 cm. Texture: Very slightly pubescent; woody at base. Color: 79A.

*Foliage description*.—Leaves alternate, single. Quantity of leaves per secondary branch: Numerous, about 20 to 24. Length, fully expanded leaves, basal: About 6 cm. Width, fully expanded leaves, basal: About 2 cm. Shape: Elliptic to lanceolate. Apex: Broadly acute. Base: Attenuate. Margin: Nearly entire with three to five widely-spaced irregular teeth. Teeth typically present an older leaves. Aspect: Mostly flat. Texture: Smooth; thick and leathery; slightly pubescent on lower surface. Color: Young foliage, upper surface: 139A. Young foliage, lower surface: 137B. Fully expanded foliage, upper surface: 139A. Fully expanded foliage, lower surface: 137B. Attenuated leaf base: 137B to 137C. Venation, upper surface: 139C. Venation, lower surface: 137C.

Inflorescence description:

*Appearance*.—Daisy-type composite inflorescence form; actinomorphic. Single inflorescences displayed above foliage, upright on long peduncles arising from leaf axils. Disc and ray florets arranged acropetally on a capitulum. Typically about 73 opened and unopened inflorescences per plant. Inflorescences last about one week. Inflorescences persistent.

*Flowering response*.—Plants flower continuously from April to October in the Northern Hemisphere.

*Fragrance*.—None detected.

*Inflorescence size*.—Diameter: About 5.5 to 6 cm. Depth (height): About 2 to 3 cm. Diameter of disc: About 1 cm.

*Inflorescence buds*.—Length: About 1.6 cm. Width: About 9 mm. Shape: Ovoid. Color: 86A.

*Ray florets*.—Length: About 3.5 cm. Width: About 8 mm. Shape: Elliptic to ligulate. Apex: Tri-dentate, minute. Base: Acute. Margin: Entire. Aspect: Flat and slightly upright. Texture: Smooth, satiny. Number of ray florets per inflorescence: About 20 in two whorls. Color: When opening, upper surface: 80A. When opening, lower surface: Central longitudinal stripe, 86A, surrounded by 85A on either side. Fully opened, upper surface: 84B; fading to 84C with subsequent development. Fully opened, lower surface: Central longitudinal stripe, 86B, surrounded by 85A on either side.

*Disc florets*.—Shape: Tubular; slightly salverform; five-lobed, fluted at apex. Number of disc florets per inflorescence: Numerous, about 67. Length: About 5 mm. Width: About 2 mm. Color: Immature: Apex, 86A; midsection, 85A. Mature: Apex, 90A; midsection, 87C.

*Phyllaries*.—Shape: Linear. Apex: Narrowly acute. Margin: Entire. Quantity and arrangement: About 20 per inflorescence; whorled. Texture: Coarse, scabrous. Color: Upper surface: 137B. Lower surface: 138C.

*Peduncle*.—Length: About 6 cm. Aspect: Moderately strong; inflorescences held above foliage. Texture: Hispid; granular, coarse. Color: 137B.

*Reproductive organs*.—Androecium: Present on disc florets only. Stamens: Five. Anther shape: Oblong. Anther size: About 1 mm. Anther color: 86A. Pollen amount: Moderate. Pollen color: 14A. Gynoecium: Present on ray and disc florets. Pistils: One. Pistil length: About 5 mm. Stigma shape: Bipartate. Stigma color: 86A. Style length: About 3 mm. Style color: 86D. Ovary color: 142D. Seed, immature: Length: About 5 mm. Diameter: About 2 mm. Color: Green.

Disease resistance: Resistance to pathogens common to Osteospermum has not been observed on plants of the new Osteospermum.

Heat tolerance: Plants of the new Osteospermum have demonstrated good tolerance to high tppemperatures.

It is claimed:

1. A new and distinct cultivar of Osteospermum plant named 'Dondo', as illustrated and described.

* * * * *

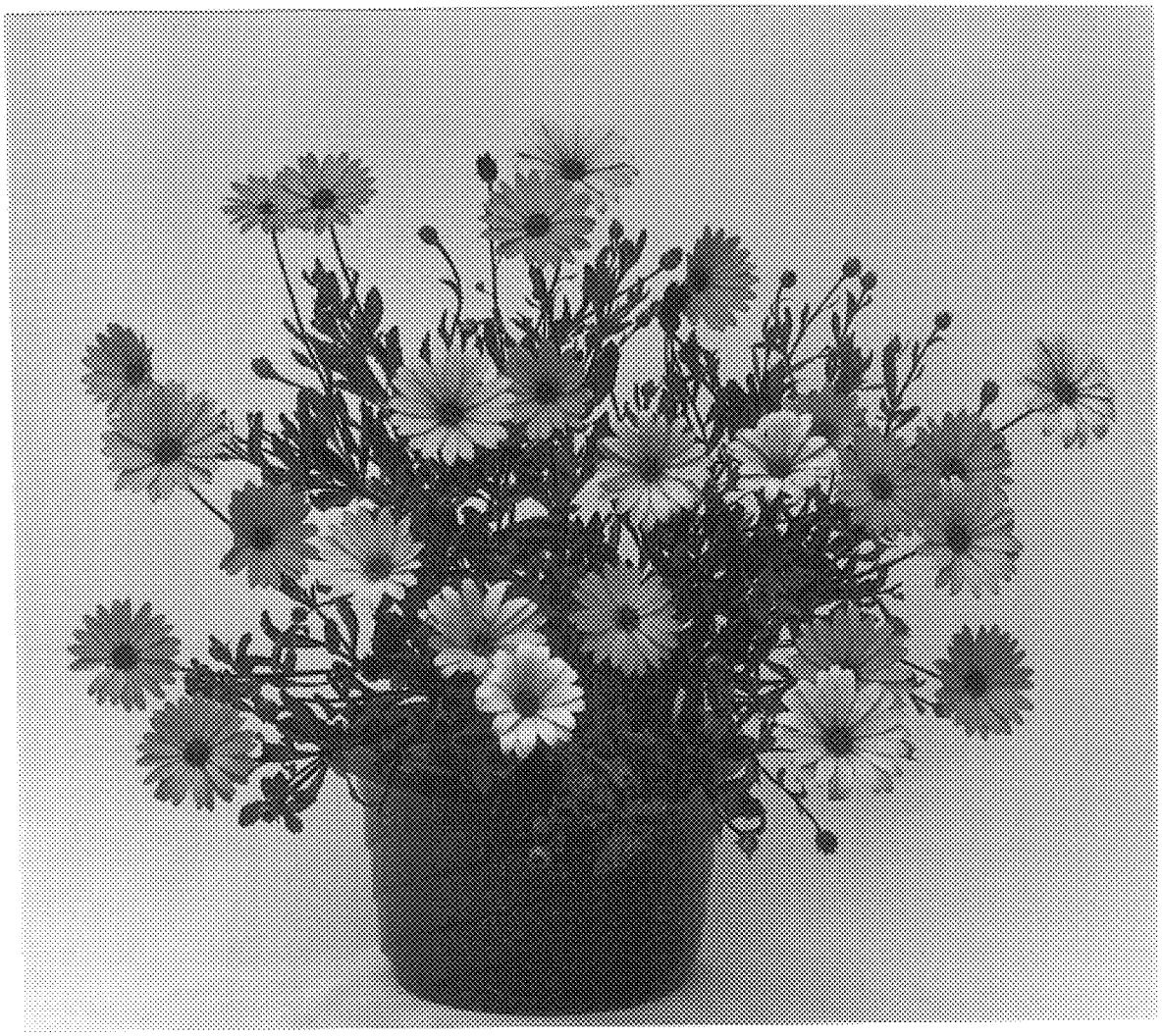
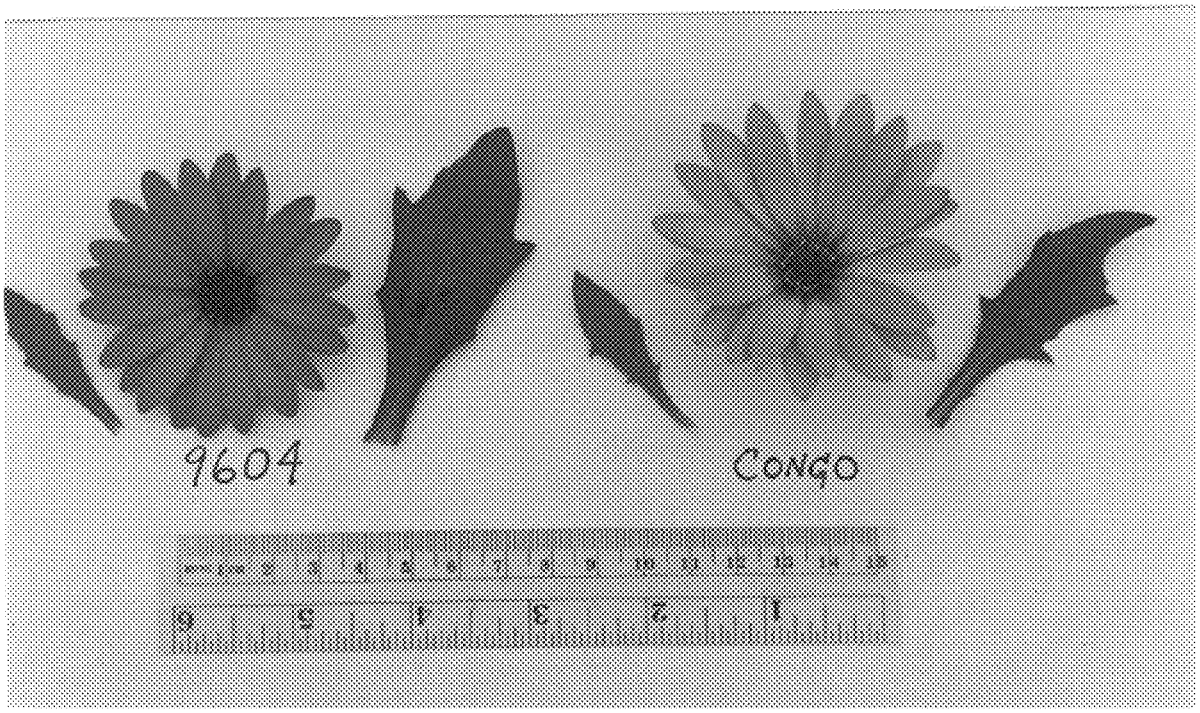
9604
CONGO